(12) United States Patent
Vetter et al.

(10) Patent No.: US 7,645,267 B2
(45) Date of Patent: Jan. 12, 2010

(54) PREFILLED SYRINGE

(75) Inventors: Udo J. Vetter, Ravensburg (DE); Joachim Glocker, Weingarten (DE); Jochen Alberstetter, Ravensburg (DE)

(73) Assignee: Arzneimittel GmbH, Ravensburg (DE)

( * ) Notice: Subject to any disclaimer, the term of this patent is extended or adjusted under 35 U.S.C. 154(b) by 457 days.

(21) Appl. No.: 10/535,760

(22) PCT Filed: Nov. 19, 2003

(86) PCT No.: PCT/EP03/12924

§ 371 (c)(1),
(2), (4) Date: Nov. 1, 2005

(87) PCT Pub. No.: WO2004/045681

PCT Pub. Date: Jun. 3, 2004

(65) Prior Publication Data

US 2006/0129108 A1   Jun. 15, 2006

(30) Foreign Application Priority Data

Nov. 21, 2002   (DE) .................. 102 54 321

(51) Int. Cl.
*A61M 5/315* (2006.01)
(52) U.S. Cl. ....................... 604/228; 604/218
(58) Field of Classification Search ................ 604/218, 604/220, 228, 110
See application file for complete search history.

(56) References Cited
U.S. PATENT DOCUMENTS 1,110,189 A   9/1914   Dodge
3,921,864 A * 11/1975   Dawes .................. 222/386
4,874,381 A * 10/1989   Vetter .................... 604/191
5,080,649 A * 1/1992   Vetter ..................... 604/91
5,456,388 A   10/1995   Barnes et al.
5,688,252 A * 11/1997   Matsuda et al. ........... 604/218
5,728,075 A * 3/1998   Levander ................. 604/211
5,833,653 A * 11/1998   Vetter et al. .............. 604/82
6,331,173 B1   12/2001   Ljungquist

FOREIGN PATENT DOCUMENTS

| DE | 195 37 163 C1 | 1/1997 |
|----|---------------|--------|
| DE | 196 38 940 C2 | 4/1998 |
| DE | 102 47 963 A1 | 5/2004 |
| DE | 102 47 965 A1 | 5/2004 |
| WO | 93/14799      | 8/1993 |
| WO | 00/16829 A    | 3/2000 |

* cited by examiner

*Primary Examiner*—Nicholas D Lucchesi
*Assistant Examiner*—Aarti Bhatia Berdichevsky
(74) *Attorney, Agent, or Firm*—Harness, Dickey & Pierce, P.L.C.

(57) ABSTRACT

A prefilled medical syringe includes a syringe barrel. A syringe plunger is disposed in the barrel and displaceable by means of a plunger rod. An end plug closes off a cannula side of the syringe barrel. The plug is provided with a through-channel closed off by a membrane. A finger support is disposed at the end of the syringe barrel opposite the end plug and provided with a through-opening for the plunger rod. A thread system cooperates with the plunger rod and the finger support. The thread system includes a thread sleeve detachably connected with the finger support. The thread sleeve is provided with an inner thread that cooperates with an outer thread on the plunger rod.

21 Claims, 2 Drawing Sheets

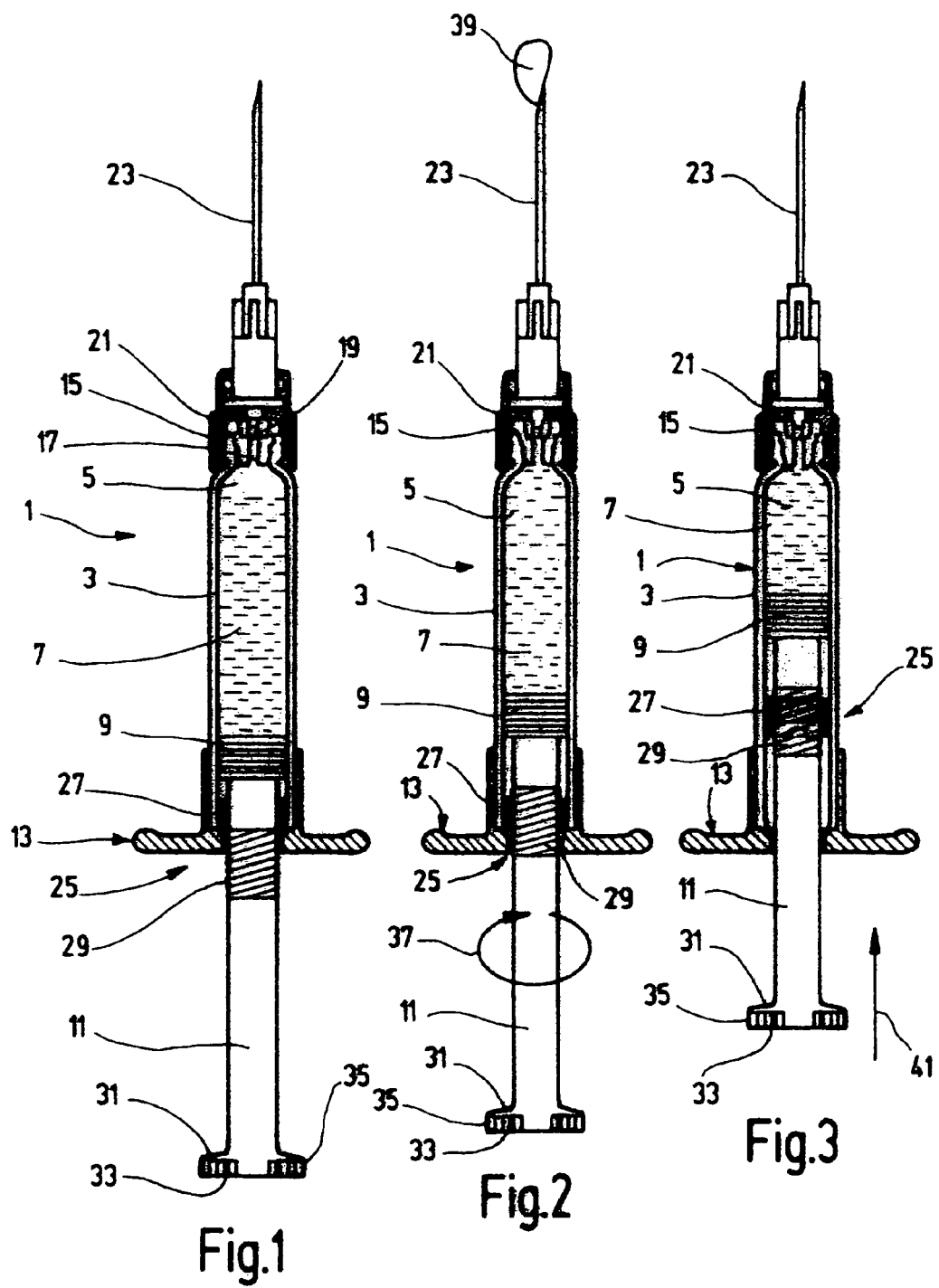

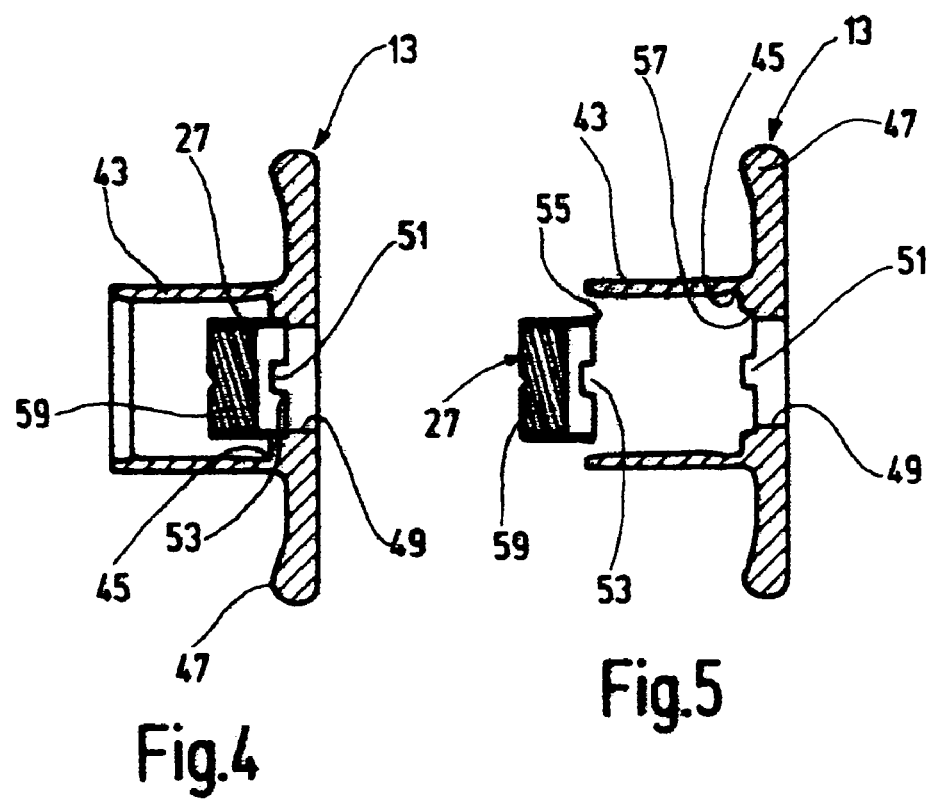
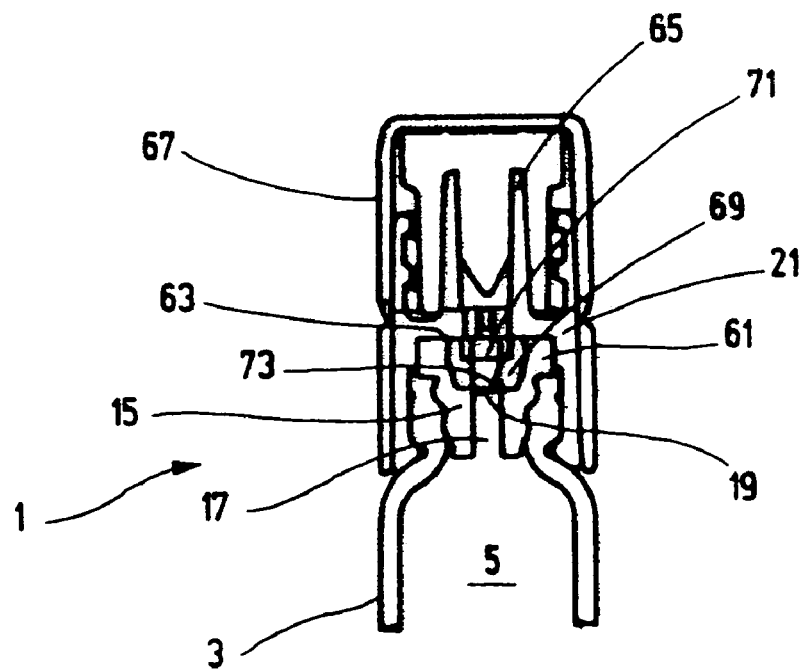

PREFILLED SYRINGE

The invention relates to a prefilled syringe for medical purposes with a syringe barrel, a syringe plunger disposed therein and displaceable by means of a plunger rod, with an end plug closing off the cannula end of the syringe barrel and provided with a through-channel closable by a membrane, with a finger support disposed at the end of the syringe barrel opposite the end plug and having a through-hole for the plunger rod, and with a thread system that cooperates with the plunger rod and the finger support.

Syringes of the kind addressed here are known (DE 196 38 940 C2). Their characterizing feature is that the inner space of the syringe barrel is tightly closed off by the membrane in the end plug. For the syringe contents to be delivered, the membrane must be ruptured. This is brought about by the pressure created in the syringe barrel as a result of the displacement of the syringe plunger which finally causes the membrane to burst. It is also known to provide a pin disposed so that when the membrane is deflected it is pierced by the pin, and the syringe contents can be delivered through a cannula. It is also known to provide a thread system that permits a defined advance of the plunger rod and of the syringe plunger connected therewith. For this purpose, the plunger rod is provided with an outer thread that cooperates with an inner thread disposed in the region of the finger support.

We have found that the point in time at which the membrane is pierced is not always exactly reproducible. Sometimes the membrane does not burst even when the plunger rod has been displaced over the entire extension of the thread. Sometimes the membrane bursts too early, namely when the thread of the plunger rod is still engaged in the thread in the finger support. It is then necessary to turn the plunger rod further until the outer thread of the plunger rod has been screwed completely through the inner thread of the finger support. Only then is the plunger rod detached from the finger support and becomes axially displaceable. Only then can the plunger rod be displaced and deliver the contents of the syringe barrel.

The object of the invention is therefore to provide a prefilled syringe of the afore-said kind that does not have this drawback.

To reach this objective, we propose a prefilled syringe. It is characterized in that the thread system is provided with a thread sleeve having an inner thread and which is detachably connected to the finger support, said inner thread cooperating with an outer thread on the plunger rod. The thread system makes it possible to turn the plunger rod so that said rod is displaced into the inner space of the syringe barrel whereby the syringe plunger is also displaced in the direction of the cannula side of the of syringe barrel. This creates pressure inside the syringe barrel causing the membrane to bulge out. Once said membrane bursts, the turning movement of the plunger rod can be discontinued. Said rod can now be subjected to a force acting in the direction of the plunger rod to displace the plunger rod inside the syringe barrel. If the outer thread of the plunger rod is still engaged with the inner thread of the thread sleeve, said sleeve can be pushed out of the finger support by the force acting in the direction of the plunger rod. By the fact that the finger support is not rigidly coupled with the plunger rod, the axial movement to advance the plunger rod and the syringe plunger can take place even if the membrane bursts at a point in time at which the outer thread of the plunger rod is still engaged in the inner thread of the thread sleeve.

Other advantages will become apparent from the subclaims.

In the following, the invention will be explained in greater detail by reference to the drawings of which:

FIG. 1 shows a longitudinal cross-section of the syringe in a first functional position;

FIG. 2 shows the syringe of FIG. 1 in a second functional position,

FIG. 3 shows the syringe represented in FIGS. 1 and 2 in a third functional position, FIG. 4 shows an enlarged view of a finger support in longitudinal cross-section, FIG. 5 shows an exploded view of the finger support of FIG. 4 in longitudinal cross-section, and FIG. 6 shows an enlarged view of the closed-off cannula end of a syringe in longitudinal cross-section.

Syringe 1 shown in FIG. 1 has a hollow syringe barrel 3 the inner space 5 of which is filled with a substance 7 provided for an injection. In inner space 5 is disposed a syringe plunger 9 that is movable in the longitudinal direction of syringe barrel 3. In a known manner, the outer diameter of the elastic syringe plunger is somewhat greater than the inner diameter of syringe barrel 3 so that, on the one hand, inner is space 5 is tightly closed off by syringe plunger 9 and, on the other, when syringe plunger 9 is displaced, substance 7 cannot leave inner space 5, which results in a pressure build-up.

Syringe plunger 9 is coupled with a plunger rod 11. Said rod passes through a finger support 13 which is firmly coupled with syringe barrel 3, for example by means of a click-stop arrangement. At the cannula-side end of syringe barrel 3 opposite finger support 13 there is provided an end plug 15 with a through-channel 17 which is closed off by a membrane 19.

End plug 15 is inserted in the known manner into the tapered end of syringe barrel 3 and is held by a cap 21 into which is inserted a cannula 23.

At the end of syringe 1 opposite cannula 23, there is provided a thread system 25 whereby plunger rod 11 is uncoupled from finger support 13. Thread system 25 comprises a thread sleeve 27 which is detachably connected with finger support 13 and is provided with an inner thread that engages in an outer thread 29 provided on the outside of plunger rod 11.

The free-standing end 31 of plunger rod 11 facing away from cannula 23 can be provided with a pressure plate 33 which on its peripheral surface is provided with knurling 35 to make the gripping of plunger rod 11 easier. This facilitates the turning of plunger rod 11 relative to the syringe barrel.

The syringe shown in FIG. 1 is in a first functional position in which syringe plunger 9 is in its starting position, namely at a maximum distance from end plug 15.

In this functional position, as a rule, inner space 5 is not under pressure so that membrane 19 is not under stress and is not bulged out. A gas-filled or air-filled free space can still be present above substance 7 in inner space 5 of syringe barrel 3.

In this functional position, outer thread 29 of plunger rod 11 is preferably not yet engaged in the inner thread of thread sleeve 27. To bring about this engagement, it is possible to displace plunger rod 11 slightly in the axial direction of syringe 1 toward cannula 23. As a result, the gas present above substance 7 in inner space 5 is compressed somewhat. This design has the ad-vantage that in the event of an unintentional turning of plunger rod 11, said rod will not be readily displaced in the axial direction of syringe barrel 3.

It is also conceivable, however, that even in the functional position of FIG. 1 outer thread 29 is engaged in the inner thread of thread sleeve 27. Unintentional displacement of plunger rod 11 can in this case be prevented in another way.

Finally, it is also possible to provide in the finger support itself a short thread, on the one hand for the purpose of introducing plunger rod 11 into finger support 13 during the assembly of syringe 1 and, on the other hand, to serve as protection against unintentional displacement of plunger rod 11 relative to finger support 13. This simple method of preventing an unintentional axial dis-placement of plunger rod 11 constitutes an essential safety factor.

FIG. 2 shows the syringe of FIG. 1 in a second functional position. Equal parts are referred to by the same reference numerals. To avoid repetition, the reader is therefore referred to the description of FIG. 1.

The second functional position according to FIG. 2 is characterized by the fact that when plunger rod 11 is turned in the direction of arrow 37, outer thread 29 of plunger rod 11 meshes with the inner thread of thread sleeve 27 and plunger rod 11 is displaced inside syringe barrel 3. Syringe plunger 9 which is coupled with plunger rod 11 is thereby pushed in the direction of cannula 23. This generates pressure in free space 5. As a result, membrane 19 bulges outward, namely in the direction of cannula 23 and is finally pierced by the inner pressure. The piercing of the membrane can be heard and felt, because the force needed to turn plunger rod 11 is markedly reduced. On further turning of plunger rod 11, syringe plunger 9 moves further in the direction of cannula 23, the gas present in inner space 5 is driven out and syringe 1 is freed of air, as defined. Finally, a drop 39 of substance 7 can emerge from cannula 23 making it clear to the user that membrane 19 was torn and that syringe 1 was deaerated. As can be seen, thread system 25 makes it possible to deaerate syringe 1 accurately and very sensitively in a simple manner.

FIG. 2 shows that in the exemplary embodiment of syringe 1 in the second functional position as shown here, the outer thread of plunger rod 11 is still engaged in the inner thread of thread sleeve 27. In other words, here an axial coupling between plunger rod 11 and finger support 13 still exists. Because finger support 13 is firmly connected with syringe barrel 3, with such coupling plunger rod 11 can, in principle, not be displaced further in the direction of cannula 23. In this case, however, thread system 25 is provided with a thread sleeve 27 which is detachably connected to finger support 13. By the pressure acting on plunger rod 11 in the direction of cannula 23, thread sleeve 27 can be separated from finger support 13 and, hence, plunger rod 11 together with syringe plunger 9 can be pushed into inner space 5 of syringe barrel 3 to deliver substance 7 through cannula 23.

FIG. 3 shows syringe 1 in its third functional position in which, by a force indicated by arrow 41, plunger rod 11 together with syringe plunger 9 is displaced in the direction of cannula 23. It can be seen clearly that the thread sleeve 27 was displaced into inner space 5 separate from finger support 13 and together with plunger rod 11.

In FIG. 3, parts previously explained in reference to FIGS. 1 and 2 are provided with the same reference numerals so that in this respect a repetition of the description was omitted.

FIG. 4 shows a magnified view of finger support 13 together with thread sleeve 27. Both parts are shown in longitudinal cross-section.

From this representation, it can be seen that the finger support can be provided with a cylindrical shoulder 43 surrounding the end of syringe barrel 3 facing away from cannula 23 and which is provided with an internal annular groove 45 into which an annular ridge extending all around can engage at the end of syringe barrel 3. In this manner, finger support 13 is safely held on syringe barrel 3.

The finger support is provided with a finger plate 47 with a through-opening 49 which as a rule is concentric with the central axis of syringe barrel 3 and through which passes plunger rod 11, not shown here. Inside cylindrical shoulder 43 is located thread sleeve 27 of thread system 25. Said sleeve constitutes a separate part and is detachably connected to finger support 13.

In principle, it is possible to press thread sleeve 27 into finger plate 47 thus anchoring it there. In the exemplary embodiment shown here, however, thread sleeve 27 is provided with an annular ridge that engages into an annular groove provided in finger plate 47. This results in an improved hold of thread sleeve 27 in finger plate 47.

To ensure that thread sleeve 27 will not turn relative to finger support 13, it may be sufficient—as previously stated—to press the thread sleeve into the base of finger support 13, particularly when, for example, the annular ridge of the thread sleeve 27 is provided with knurls that engage in the annular groove provided in finger plate 47.

Preferably provided here, however, is positive locking brought about by a projection 51 extending from finger plate 47 and engaging in groove 53 provided in thread sleeve 27. Conversely, positive locking can also be achieved by providing a projection on thread sleeve 27 that engages in a groove of finger plate 47. Moreover, it is possible to provide several projections and grooves to ensure that relative rotation between thread sleeve 27 and finger support 13 is prevented.

FIG. 5 shows an exploded view of finger plate 13 shown in FIG. 4. Equal parts are indicated by the same reference numerals, the reader therefore being referred to the explanation provided for FIG. 4. From the exploded view it is clear that on its outside thread sleeve 27 is provided with an annular ridge 55 which engages in an annular groove 57 of finger plate 47. This representation also shows clearly projection 51, which serves as positioning cam and the corresponding recess in thread sleeve 27 referred to as groove 53, From the representation according to FIGS. 4 and 5 it can be seen that the height of inner thread 59 is chosen so that said thread extends over the entire inner space of thread sleeve 27.

The height of inner thread 59 is chosen so that thread system 25 can exert sufficient force to displace syringe plunger 9 in inner space 5 and to build up an internal pressure causing membrane 19 to burst.

FIG. 6 shows an enlargement of the cannula side of syringe 1. Equal parts are indicated by the same reference numerals, the reader therefore being referred to the description of the preceding figures.

The enlargement shows in particular the end plug 15 which is inserted into the end region of syringe barrel 3 and is kept there by an appropriate positive lock. The enlargement also shows an annular shoulder 61 disposed on the front side of syringe barrel 3 and held by an appropriate support shoulder 63 of cap 21.

On the free end 65 of cap 21 is disposed a tip cap held in this position by an originality-attesting closure 67.

The inside of end plug 15 contains an insert 69 preferably consisting of a plastic material and surrounding a filter 71 through which substance 7 present inside syringe 1 is delivered.

FIG. 6 clearly shows that through-channel 17 in end plug 15 is closed off by membrane 19 and that it extends through insert 69. Here, at a distance above the membrane, can be seen projecting into through-channel 17 a pin 73 the tip of which is oriented in the direction of membrane 19. Said pin is disposed so that it pierces membrane 19 when said membrane bulges upward, namely in the direction of the cannula to be inserted, as a result of pressure from inner space 5 of syringe barrel 3. This design permits very much more accurately reproducible bursting of membrane 19 when pressure develops in inner space 5.

In the following, the function of syringe 1 will be discussed in greater detail.

The prefilled syringe 1 contains a substance 7 which by membrane 19 is tightly sealed off in inner space 5 of syringe barrel 3. After syringe 1 has been prepared, plunger rod 11 is in its withdrawn position, as shown in FIG. 1. Syringe 1 is provided with a thread system 25 which makes it possible, by turning plunger rod 11, to displace said rod in the axial direction and to move syringe plunger 9 in inner space 5 in the direction of end plug 15.

Thread system 25 is preferably configured so that plunger rod 11 in the first functional position as seen in FIG. 1 is freely turnable without the outer thread 29 of plunger rod 11 being engaged in the inner thread 59 of thread sleeve 27 in finger support 13. Activation of thread system 25 occurs when plunger rod 11 is pressed slightly into syringe barrel 3 so that the two thread regions engage in each other.

Thread system 25 then brings about, as shown in FIG. 2, a displacement of syringe plunger 9 which causes pressure to be generated in inner space 5, said pressure causing membrane 19 to bulge out in the direction of cannula 17. In a first preferred embodiment, the bulging alone causes membrane 19 to burst when plunger rod 11 is screwed further into syringe barrel 3. It is also possible, however, as was explained by reference to FIG. 6, to provide in the immediate vicinity of membrane 19 a pin 73 which when the membrane is caused to bulge makes a tear in it leading to the defined bursting. Thread system 25 is configured so that in finger support 13 the turning motion of plunger rod 11 is decoupled from an axial movement of plunger rod 11 in inner space 5 of syringe barrel 3. The advantage of this is that after the bursting of membrane 19 and optionally after the deaeration of inner space 5 the axial displacement of the plunger rod can be carried out independently of the instantaneous position of outer thread 29 in inner thread 59: As shown in FIG. 3, when pressure is exerted on plunger rod 11 in the direction of arrow 41, thread sleeve 27 is detached from finger plate 47 in finger support 13 so that plunger rod 11 together with syringe plunger 9 is freely movable independently of thread system 25. This design ensures that the axial decoupling of plunger rod 11 from finger support 13 no longer depends on the system accuracy and on tolerances specified for the fabrication of the syringe.

The function of thread system 25 is also ensured by the fact that here thread sleeve 27 finds reliable support in finger plate 47 where it is held in rotation-resisting manner. This can be achieved by means of a force fit or by a positive lock explained in greater detail by reference to FIGS. 4 and 5. Preferably, by engagement of a projection 51 extending from finger plate 47, thread sleeve 27 is held in groove 53 provided on thread sleeve 27.

Thread system 25 is a separate part, namely separated from finger support 13 and plunger rod 11, and is designed so that syringes 1 can also be retrofitted with said system provided said syringes are equipped with a plunger rod 11 having an outer thread 29.

It is clear from all this that in syringe 1 explained here, finger support 13 itself does not have an inner thread but that it consists of two parts. Said support comprises a thread sleeve 27 of a thread system 25 which as a separate part is detachably connected to finger support 13 so that the turning motion of plunger rod 11 is completely separated from its axial movement. Even when the outer thread of plunger rod 11 still mates with the inner thread 59 of thread sleeve 27, plunger rod 11 can be displaced in axial direction. In other words, the turning motion of plunger rod 11 occurs only until membrane 19 is reliably pierced and the inner space 5 of syringe 1 is deaerated.

The fact that during the axial insertion of plunger rod 11 into inner space 5 the thread sleeve is separated from finger support 13 provides additional safety in the use of syringe 1: By turning plunger rod 11 back, thread sleeve 47 can no longer be returned to its starting position. A new use of syringe 1 is thus made impossible. In other words, a contaminated syringe is thus prevented from being reused. This ensures that the syringe can be used only once.

The invention claimed is:

1. A prefilled medical syringe comprising:
a syringe barrel enclosing an inner space;
a syringe plunger disposed in the space and coupled to a first end of a plunger rod, the plunger rod having an outer thread that is formed between the first end and a second end and a non-threaded portion disposed between the outer thread and the first end;
an end plug closing off a cannula end of the syringe barrel, the end plug having a through-channel closed off by a membrane;
a finger support disposed on an end of the syringe barrel opposite the end plug and having a through-opening for the plunger rod; and
a thread system that cooperates with the plunger rod and with the finger support, the thread system having a thread sleeve with an inner thread that cooperates with the outer thread on the plunger rod to move the plunger rod relative to the syringe barrel,
wherein the thread sleeve is attached to the finger support prior to the outer thread of the plunger rod meshing with the inner thread of the thread sleeve; and
wherein movement of the plunger rod and the thread sleeve relative to the syringe barrel causes the thread sleeve to be disconnected from the finger support.

2. The syringe of claim 1, wherein the plunger rod and thread sleeve move relative to the syringe barrel when the outer thread of the plunger rod meshes with the inner thread of the thread sleeve.

3. The syringe of claim 1, wherein the thread sleeve is coupled with the finger support in a positively locking manner.

4. The syringe of claim 1, wherein the thread system is configured as a separate part.

5. The syringe of claim 1, wherein the thread sleeve is pressed into the base of the finger support.

6. The syringe of claim 1, wherein rotation of the plunger rod into meshed engagement with the inner thread of the thread sleeve causes the plunger rod to be displaced and move toward the cannula.

7. The syringe of claim 1, wherein the thread sleeve is operable to receive the non-threaded portion of the plunger rod prior to the outer thread of the plunger rod meshing with the inner thread of the thread sleeve.

8. The syringe of claim 1, further comprising a pin in selective engagement with the membrane.

9. The syringe of claim 8, wherein the engagement of the inner thread and outer thread increases the pressure in the inner space.

10. The syringe of claim 9, wherein the increase in pressure causes the membrane to bulge and contact the pin that ruptures the membrane.

11. A prefilled medical syringe comprising:

a syringe barrel enclosing an inner space;

a syringe plunger disposed in the space and coupled to a first end of a plunger rod, the plunger rod having an outer thread that is formed between the first end and a second end and a non-threaded portion disposed between the outer thread and the first end;

an end plug closing off a cannula end of the syringe barrel, the end plug having a through-channel closed off by a membrane;

a finger support disposed on an end of the syringe barrel opposite the end plug and having a through-opening for the plunger rod; and a thread system that cooperates with the plunger rod and with the finger support, the thread system having a thread sleeve with an inner thread that cooperates with the outer thread on the plunger rod to move the plunger rod relative to the syringe barrel;

wherein the plunger rod and thread sleeve move relative to the syringe barrel when the outer thread of the plunger rod meshes with the inner thread of the thread sleeve.

12. The syringe of claim 11, wherein the thread sleeve is attached to the finger support prior to the outer thread of the plunger rod meshing with the inner thread of the thread sleeve.

13. The syringe of claim 12, wherein movement of the plunger rod and the thread sleeve relative to the syringe barrel causes the thread sleeve to be disconnected from the finger support.

14. The syringe of claim 11, wherein the thread sleeve is coupled with the finger support in a positively locking manner.

15. The syringe of claim 11, wherein the thread system is configured as a separate part.

16. The syringe of claim 11, wherein the thread sleeve is pressed into the base of the finger support.

17. The syringe of claim 11, wherein rotation of the plunger rod into meshed engagement with the inner thread of the thread sleeve causes the plunger rod to be displaced and move toward the cannula.

18. The syringe of claim 11, wherein the thread sleeve is operable to receive the non-threaded portion of the plunger rod prior to the outer thread of the plunger rod meshing with the inner thread of the thread sleeve.

19. The syringe of claim 11, further comprising a pin in selective engagement with the membrane.

20. The syringe of claim 19, wherein the engagement of the inner thread and outer thread increases the pressure in the inner space.

21. The syringe of claim 20, wherein the increase in pressure causes the membrane to bulge and contact the pin that ruptures the membrane.

* * * * *

UNITED STATES PATENT AND TRADEMARK OFFICE
CERTIFICATE OF CORRECTION

PATENT NO. : 7,645,267 B2 Page 1 of 1
APPLICATION NO. : 10/535760
DATED : January 12, 2010
INVENTOR(S) : Udo J. Vetter et al.

It is certified that error appears in the above-identified patent and that said Letters Patent is hereby corrected as shown below:

On the Title Page, item (73), Assignee should appear as follows: Arzneimittel GmbH --Apotheker Vetter & Co.--

Signed and Sealed this

Sixteenth Day of March, 2010

David J. Kappos
*Director of the United States Patent and Trademark Office*